(12) United States Patent
Bächler et al.

(10) Patent No.: US 11,179,511 B2
(45) Date of Patent: Nov. 23, 2021

(54) MEDICAL SUCTION PUMP

(71) Applicant: MEDELA HOLDING AG, Baar (CH)

(72) Inventors: Cornel Bächler, Honau (CH); Armin Felber, Lucerne (CH); Marcel Muther, Ebikon (CH)

(73) Assignee: MEDELA HOLDING AG, Baar (CH)

( * ) Notice: Subject to any disclaimer, the term of this patent is extended or adjusted under 35 U.S.C. 154(b) by 345 days.

(21) Appl. No.: 16/075,559

(22) PCT Filed: Mar. 2, 2017

(86) PCT No.: PCT/EP2017/054970
§ 371 (c)(1),
(2) Date: Aug. 3, 2018

(87) PCT Pub. No.: WO2017/157691
PCT Pub. Date: Sep. 21, 2017

(65) Prior Publication Data
US 2019/0365966 A1 Dec. 5, 2019

(30) Foreign Application Priority Data

Mar. 17, 2016 (EP) .................................. 16160970

(51) Int. Cl.
*A61M 1/00* (2006.01)
*A61M 1/04* (2006.01)
(Continued)

(52) U.S. Cl.
CPC ................ *A61M 1/80* (2021.05); *A61M 1/04* (2013.01); *A61M 1/06* (2013.01); *A61M 1/90* (2021.05);
(Continued)

(58) Field of Classification Search
CPC ........ A61M 1/04; A61M 1/06; A61M 1/0066; A61M 1/0088; A61M 2205/42; F04B 39/0044
See application file for complete search history.

(56) References Cited

U.S. PATENT DOCUMENTS

2007/0292276 A1   12/2007   Stutz et al.
2008/0275386 A1   11/2008   Myers
(Continued)

FOREIGN PATENT DOCUMENTS

CN    202342540 U     7/2012
DE    102012101642 A1  8/2013
(Continued)

OTHER PUBLICATIONS

International Search Report for Application No. PCT/EP2017/054970, dated Jun. 2, 2017.

*Primary Examiner* — Nathan R Price
*Assistant Examiner* — Justin L Zamory
(74) *Attorney, Agent, or Firm* — Marshall, Gerstein & Borun LLP

(57) ABSTRACT

A medical suction pump has a pump housing, a pump assembly arranged in the pump housing and serving to generate an underpressure, and a device for sound damping. The device for sound damping has at least two elastic bearings for elastically supporting the pump assembly relative to the pump housing, wherein the bearings are arranged spaced apart from each other. By virtue of the flexible support, the suction pump permits optimal sound damping.

21 Claims, 6 Drawing Sheets

(51) Int. Cl.
    *A61M 1/06*      (2006.01)
    *F04B 39/00*     (2006.01)
(52) U.S. Cl.
    CPC ..... *F04B 39/0044* (2013.01); *A61M 2205/42* (2013.01); *F05C 2225/00* (2013.01)

(56) References Cited

U.S. PATENT DOCUMENTS

2011/0017544 A1\* 1/2011 Bodwell ................ F04B 35/06
                                                    181/200
2015/0027561 A1\* 1/2015 Mauthe ................. A61C 17/04
                                                    137/377

FOREIGN PATENT DOCUMENTS

| | | |
|---|---|---|
| KR | 101462340 B1 | 11/2014 |
| WO | WO-2007/122578 A1 | 11/2007 |
| WO | WO-2015/109934 A1 | 7/2015 |
| WO | WO-2016/103031 A1 | 6/2016 |

\* cited by examiner

MEDICAL SUCTION PUMP

The present application is the US national phase of International Application No. PCT/EP2017/054970, filed Mar. 2, 2017, which claims priority to European Application No. 16160970.6, filed Mar. 17, 2016. The priority, EP 16160970.6, is hereby incorporated by reference in its entirety.

TECHNICAL FIELD

The present invention relates to a medical suction pump, in particular a breast pump for expressing human breastmilk or a drainage pump for aspirating body liquids, for example for chest drainage or for wound drainage.

PRIOR ART

Medical suction pumps, also called vacuum pumps, are known for a wide variety of uses. For example, they are used as breast pumps for expressing human breastmilk or as drainage pumps for aspirating body liquids. Such suction pumps have piston pumps or diaphragm pumps as a pump assembly. The use of a pump diaphragm means that the suction pump can be made relatively small and light and therefore portable during use. A pump assembly that is very small but nevertheless satisfies the strict demands placed on a breast pump is disclosed, for example, in US 2007/0292276.

Many of these pumps have the disadvantage of being relatively noisy. They are difficult to use discreetly in public and/or they disturb the user on account of the rhythmically recurring noises.

WO 2015/109934 A1 discloses a breast pump with sound damping. The pump assembly is held in a closed internal housing, wherein the hollow space between the inner wall of the housing and the pump assembly is filled with shock absorbers made of foam. The internal housing has two halves, which are connected to each other by a silicone ring. This internal housing is fixed with screws in a breast pump housing, wherein three shock absorbers arranged on the outer face of the internal housing reduce the transmission of vibrations of the pump assembly to the external pump housing. This complete encapsulation of the pump assembly with foam has the disadvantage that heat generated in the assembly can be removed only very poorly. Moreover, this foam cushion requires quite a lot of space and provides only moderate damping of structure-borne sound.

KR 101462340 B1 describes a breast pump with sound damping. A pump housing made of metal is designed with a sound-damping mat, and the pump assembly is inserted with an exact fit. A sound-damping edge is likewise provided between the cover part and base part of the housing.

CN 202342540 U discloses a vertical arrangement of the pump assembly, with a damping element arranged on the vacuum port of the pump assembly.

DISCLOSURE OF THE INVENTION

It is therefore an object of the invention to make available a medical suction pump which can be operated with the least possible noise and which nonetheless permits very great flexibility in the design of the pump.

The medical suction pump according to the invention has a pump housing, a pump assembly arranged in the pump housing and serving to generate an underpressure, and a device for sound damping. The device for sound damping has at least two elastic bearings for elastically supporting the pump assembly relative to the pump housing, which bearings are arranged spaced apart from each other.

The elastic suspension and support prevents transmission of vibrations and structure-borne sound from the pump assembly to the pump housing. By virtue of the invention, the pump assembly is held in a defined position and yet is suspended so flexibly that the noise development is reduced and/or damped.

The two-point, three-point or multi-point support at locations spaced apart from each other, i.e. discrete locations, with respect to the pump assembly, without further sound-damping elements lying in between, has the advantage that the supporting of the pump assembly inside the pump housing can be chosen relatively freely. The use of exactly three bearings forms a statically defined system.

In a simple embodiment, the bearings are arranged directly on the pump assembly, and the matching bearings are located on the pump housing itself, i.e. the pump assembly is held in the pump housing directly and without any further intermediate parts.

The sound damping is improved if the pump assembly is additionally arranged in a sound-damping housing and is supported elastically relative to the latter. The sound-damping housing forms a closed shell and thus reduces the propagation of air-borne sound. It preferably has a buffer volume for exhaust air emerging from the pump assembly. A buffer volume of this kind decreases the flow pressure and pressure surges and thus reduces the development of noise.

To ensure that pump assemblies of a known type can be used unchanged, a pump assembly carrier is preferably present, which carries the elastic bearings and which holds the pump assembly in a fixed position. Depending on the embodiment, the pump assembly carrier forms a unity or it is formed by two or more sub-unities or parts of the carrier, wherein the sub-unities or parts are spaced from each other.

The pump assembly is preferably held with pretensioning in this carrier, so that the connection between the two main parts of the pump assembly, i.e. motor and vacuum assembly, is as firm as possible and does not lead to vibrations. In preferred embodiments, the pump assembly carrier is therefore formed as a contiguous unity. This pretensioning appreciably reduces the noise development of the assembly.

Exactly two elastic bearings are preferably present, and the pump assembly is connected to the pump housing, or to the sound-damping housing arranged therebetween, exclusively via these two bearings. These exactly two bearings are preferably arranged at two opposite ends of the pump assembly. Especially, they are arranged along a longitudinal axis of the pump assembly or they are offset at equal distances on opposite sides of the longitudinal axis. Preferably, they are arranged on the center of the gravity axis of the pump assembly. Exactly three elastic bearings are preferably present, in which case the abovementioned connection is provided exclusively via these three bearings. Three-point supports are defined arrangements and make play between the individual parts impossible.

The at least two or the at least three bearings are preferably formed from an elastomer. These materials are cost-effective, can be produced in any desired shapes and, above all, are durable in use. However, there is hardly any material fatigue.

A first and a second of these bearings are preferably oriented in mutually opposite directions.

If a third bearing is present, it is preferably oriented in a further direction extending perpendicularly from said directions.

In embodiments with at least or exactly three bearings, the first and the second bearing are preferably arranged in the area of a vacuum assembly of the pump assembly, and the third bearing is preferably arranged in the area of a motor of the pump assembly. A balanced support with respect to the centre of gravity of the assembly is advantageous.

In a preferred embodiment, the at least two bearings are held insertably in bearing seats. This makes the pump easier to produce and to assemble.

The at least two bearings are preferably elastomer bodies that can be plugged on. This too makes production and assembly easier.

If a sound-damping housing is present, it is preferably designed in two parts. It is preferably closed in an airtight manner except for a first and a second air passage and except for a vacuum port.

An air exchange unit is preferably present which delivers air to the pump assembly through the first air passage of the sound-damping housing and withdraws air from the pump assembly through the second air passage of the sound-damping housing. The air exchange unit can be formed integrally on the sound-damping housing or integrally on the pump housing. However, it is preferably a separate component, which is arranged between pump housing and sound-damping housing.

The sound-damping housing is preferably arranged in a fixed position in the pump housing, wherein the air exchange unit is arranged between pump housing and sound-damping housing.

In a preferred embodiment, the air exchange unit is plate-shaped.

The air exchange unit preferably has channels with channel walls, which are designed to damp sound and are preferably pliable. This too increases the sound damping.

Exhaust air withdrawn from the pump assembly is preferably conveyed at least over part of a flow path through a tubular airstream sound damper. This reduces the airborne sound caused by edge friction of the air flowing through.

Further embodiments are set forth in the dependent claims.

BRIEF DESCRIPTION OF THE DRAWINGS

Preferred embodiments of the invention are described below with reference to the drawings, which serve only for explanatory purposes and are not to be interpreted as limiting the invention. In the drawings.

DESCRIPTION OF PREFERRED EMBODIMENTS

Figure 1:
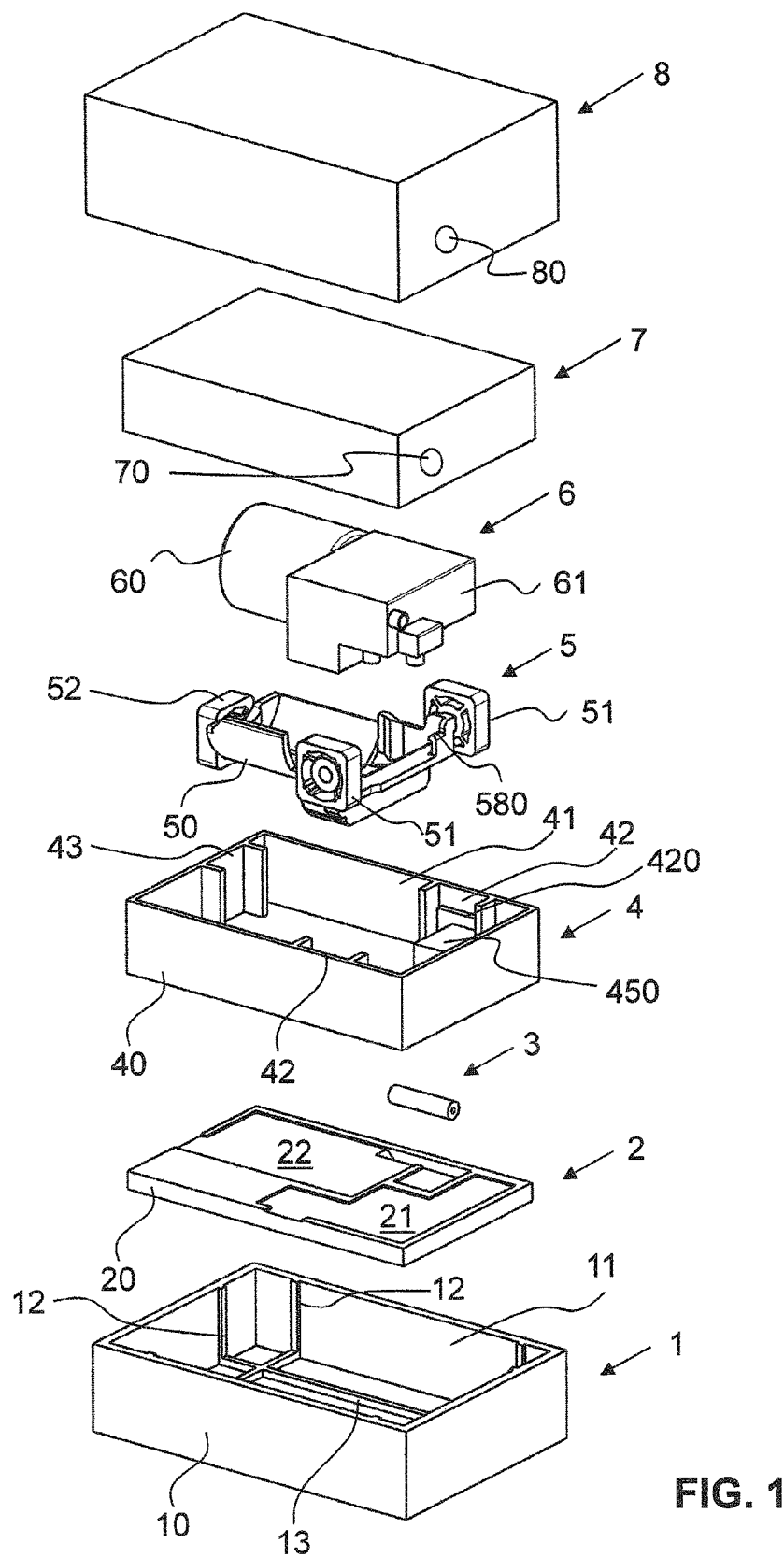
FIG. 1 shows a schematic view of a suction pump according to the invention in a first embodiment.

A medical suction pump according to the invention is shown in a schematic exploded view in FIG. 1.

The suction pump is, for example, a breast pump for expressing human breastmilk. The breast pump is connected directly, or via a vacuum hose, to one or two breastshields for placing on the mother's breast.

In another embodiment, the suction pump is a drainage pump, for example for chest drainage or wound drainage.

The suction pump preferably has a relatively small format, such that it is portable and, during use, can be worn on the body or held in one hand.

The suction pump comprises a pump housing with a first pump housing part 1 and a second pump housing part 8. A sound-damping housing is held in a fixed position in this pump housing 1, 8 and preferably likewise consists basically of a first sound-damping housing part 4 and a second sound-damping housing part 7.

A pump assembly 6 is mounted in the sound-damping housing 4, 7, it being possible for said pump assembly 6 to be secured directly on the sound-damping housing 4, 7. In this example, the pump assembly 6 is arranged in a pump assembly carrier 5, which is mounted in the sound-damping housing 4, 7. According to the invention, the pump assembly 6 and pump assembly carrier 5 are supported via at least two, preferably exactly three elastic bearings 51, 52. No further attachments or connections to the sound-damping housing 4, 7 are present. This suspension of the pump assembly 6 alone or, as shown here, together with the pump assembly carrier 5 prevents the transmission of vibrations to the sound-damping housing 4, 7 and thus to the pump housing 1, 8. The suspension is described in more detail in the text below.

The pump assembly 6 is a known unit for generating underpressure and forms the core of the vacuum pump. The pump assembly 6 usually comprises a motor 60, usually an electric motor, and a vacuum assembly 61. The vacuum assembly 61 usually has a pump chamber with a pump diaphragm, which is connected to the motor via a drive rod and is movable by means of the motor. A pump assembly of this kind is described, for example, in US 2007/0292276.

To ensure that the pump assembly 6 is provided with the air delivery and air withdrawal needed for the operation, the suction pump according to the invention has a gap system, here called an air exchange unit 2. In this example, the air exchange unit 2 is arranged between the first pump housing part 1 and the first sound-damping housing part 4 and is configured as a separate component. However, it can also be an integral component of a pump housing part 1, 8 or of a sound-damping housing part 4, 7.

Figure 2:
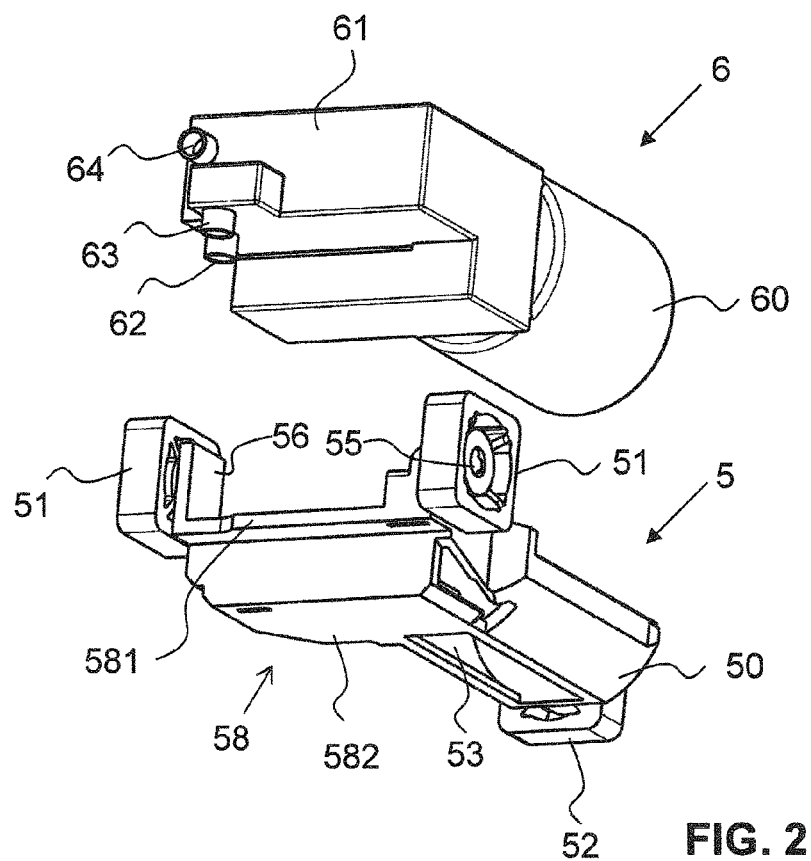
FIG. 2 shows a schematic view of a pump assembly and of a pump assembly carrier according to FIG. 1.
Figure 3:
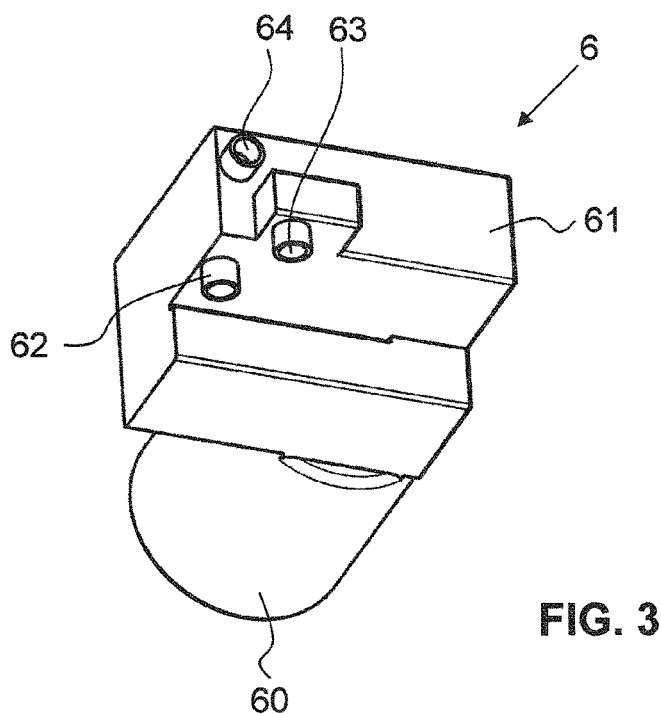
FIG. 3 shows a perspective view of the pump assembly according to FIG. 2.

The individual parts mentioned above are described in more detail below:

As can be seen clearly in FIGS. 2 and 3, the motor 60 in this example is designed as a cylinder lying horizontally. This corresponds to the usual form. The vacuum assembly 61 connected firmly thereto can have various forms. In this example, it is basically composed of two blocks. The vacuum assembly 61 has a ventilation opening 63, an exhaust air opening 62 and a vacuum port 64. The ventilation opening 63, the exhaust air opening 62 and the vacuum port 64 are designed in this example as adapters. Other configurations are possible.

The pump assembly carrier 5 is preferably produced from a stiff material. It is preferably made from plastic.

Figure 4:
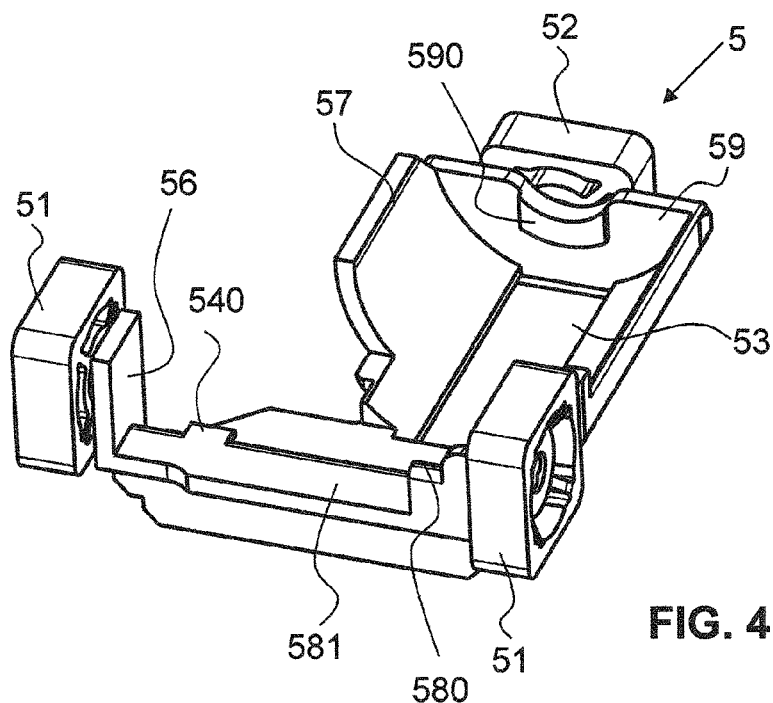
FIG. 4 shows a perspective view of the pump assembly carrier according to FIG. 2.
Figure 5:
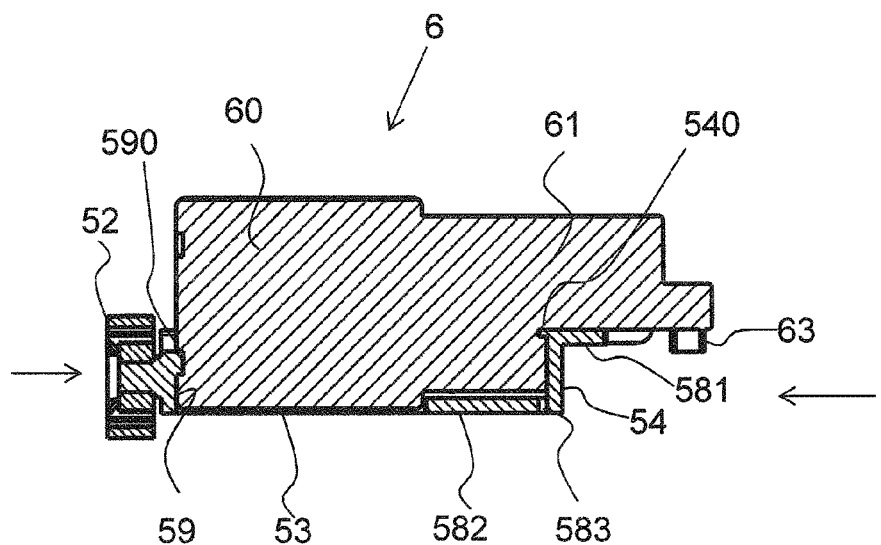
FIG. 5 shows a longitudinal section through the pump assembly carrier, with the pump assembly held therein according to FIG. 2.

As can be seen clearly in FIGS. 2 and 4, the pump assembly carrier 5 is shaped according to the shape of the pump assembly 6. It has a motor seat 50 in the form of a semicylindrical shell with a relatively wide gap 53. The motor seat 50 merges at one side into an assembly support 58. The latter, together with a surface directed towards the motor seat 50, forms a first abutment 54, as can be seen clearly in FIG. 5. The end of the motor seat 50 opposite this surface forms a second abutment 59. The first abutment 54 is provided with at least a first locking lug 540, while the second abutment 59 is provided with at least a second locking lug 590.

The bottom 582 of the assembly support 58 directed towards the motor seat 50 is provided, in a corner area, with a gap or an opening 583. The opening 583 serves to permit removal from the injection-moulding tool or to permit shaping of the first locking lug 540.

The assembly support 58 has a balcony 581 which is directed away from the motor seat 54 and which bears the vacuum assembly 61. The balcony 581 is preferably provided with a third locking lug 580 on an upwardly directed rear abutment.

By virtue of the first and second locking lugs 540, 590 and, if present, also by virtue of the third locking lug 580, the pump assembly 6 is held with pretensioning in the pump assembly carrier 5. In this way, any vibrations between motor 60 and vacuum assembly 61 during the operation of the pump are avoided and the noise development is minimized.

The assembly support 58 has, on both sides, an upwardly directed lateral abutment 56 for receiving the vacuum assembly 61, as can be seen in FIG. 2. On the outer face of these abutments 56 there is in each case an outwardly directed securing pin 55 for receiving a respective first bearing 51. The bearing 51 is elastic. It is preferably an elastomer bearing. In this example, each bearing 51 has a rounded cuboid frame, with a hollow space provided with webs. The bearing 51 can be mounted and fixed by simply being plugged onto the securing pin 55.

A further securing pin 55 is integrally formed on the free end of the motor seat 50 and carries a second elastic bearing 52, preferably likewise an elastomer bearing.

The three bearings 51, 52 are preferably identical in size, shape and elasticity. They are preferably arranged such that the forces acting during movement of the pump assembly carrier 5 together with the pump assembly 6 are uniformly distributed, i.e. such that the arrangement is held uniformly in relation to its centre of gravity.

As is shown in FIG. 1, the pump assembly carrier 5, together with the pump assembly 6 held therein with pretensioning, is suspended in an interior 41 of the first sound-damping housing part 4 by means of the elastic support.

In a first half-shell 40, which essentially forms the first sound-damping housing part 4, first bearing seats 42 are present for the first and second bearings 51, and a second bearing seat 43 is present for the third bearing 52. The bearing seats 42, 43 are each formed by two parallel and inwardly protruding side walls, into which the bearings 51, 52 can be pushed from above. The bearings 51, 52 are thereby pressed together and held in their position. Between the two side walls, the first bearing seats 42 each have a lower abutment 420, such that the pump assembly carrier 5 can be arranged horizontally in the first half-shell 40 and parallel to the bottom of the latter. Other types of the elastic support, of the suspension and of the design of the bearings, in form and arrangement, are possible within the meaning of this invention.

Figure 7:
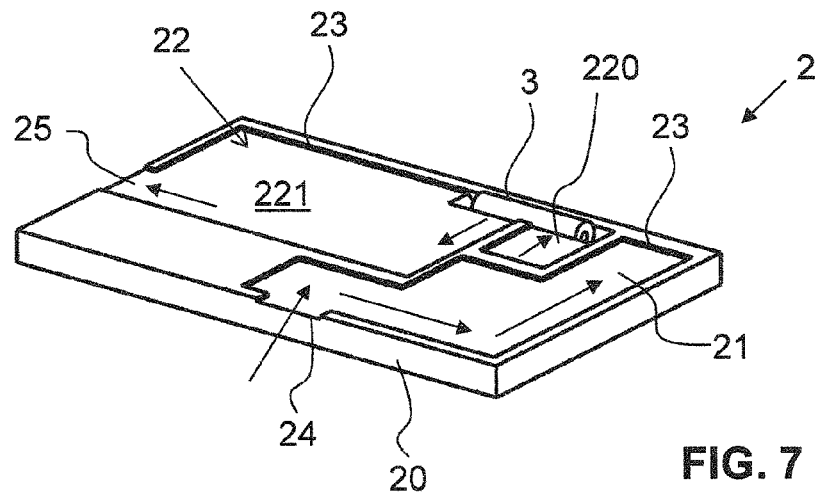
FIG. 7 shows a perspective top view of an air exchange unit according to FIG. 1.
Figure 8:
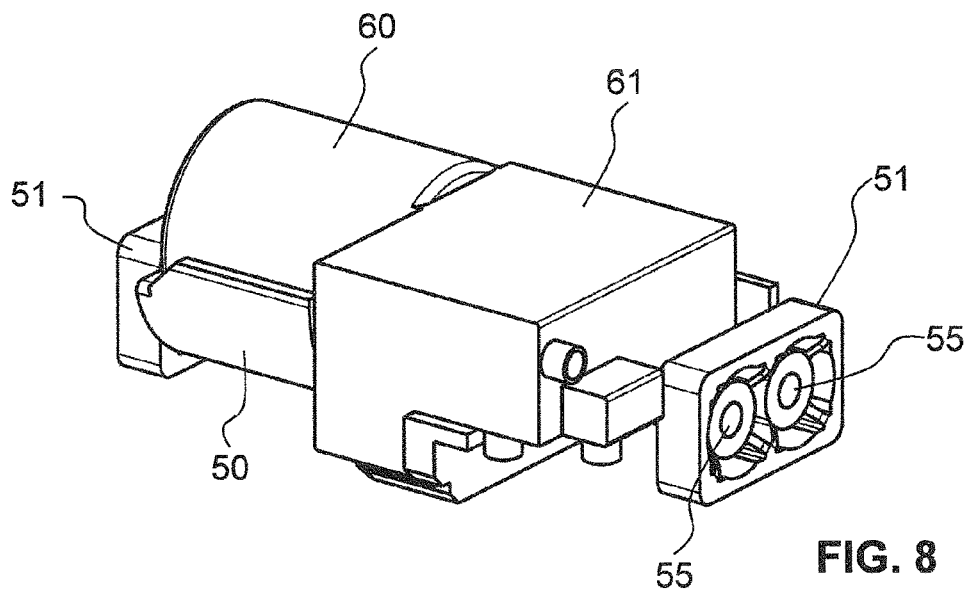
FIG. 8 shows a schematic view of a pump assembly and of a pump assembly carrier according to a second embodiment of the invention.

FIG. 8 shows an alternative embodiment. Here, there are exactly two elastic bearings 51 present, which are arranged on two opposite sides in the longitudinal direction of the pump assembly 6. They can be designed and held identically to the bearings described above. However, they can also be designed differently or at least be larger than the abovementioned bearings. In the example shown here, at least one of the two bearings 51, here the bearing 51 directed towards the vacuum assembly 61, is broader. It preferably has two web structures inside a closed frame and/or is preferably held on two securing pins 55. The other parts correspond to the embodiment according to FIGS. 1 to 7 and are not shown anymore.

Figure 9:
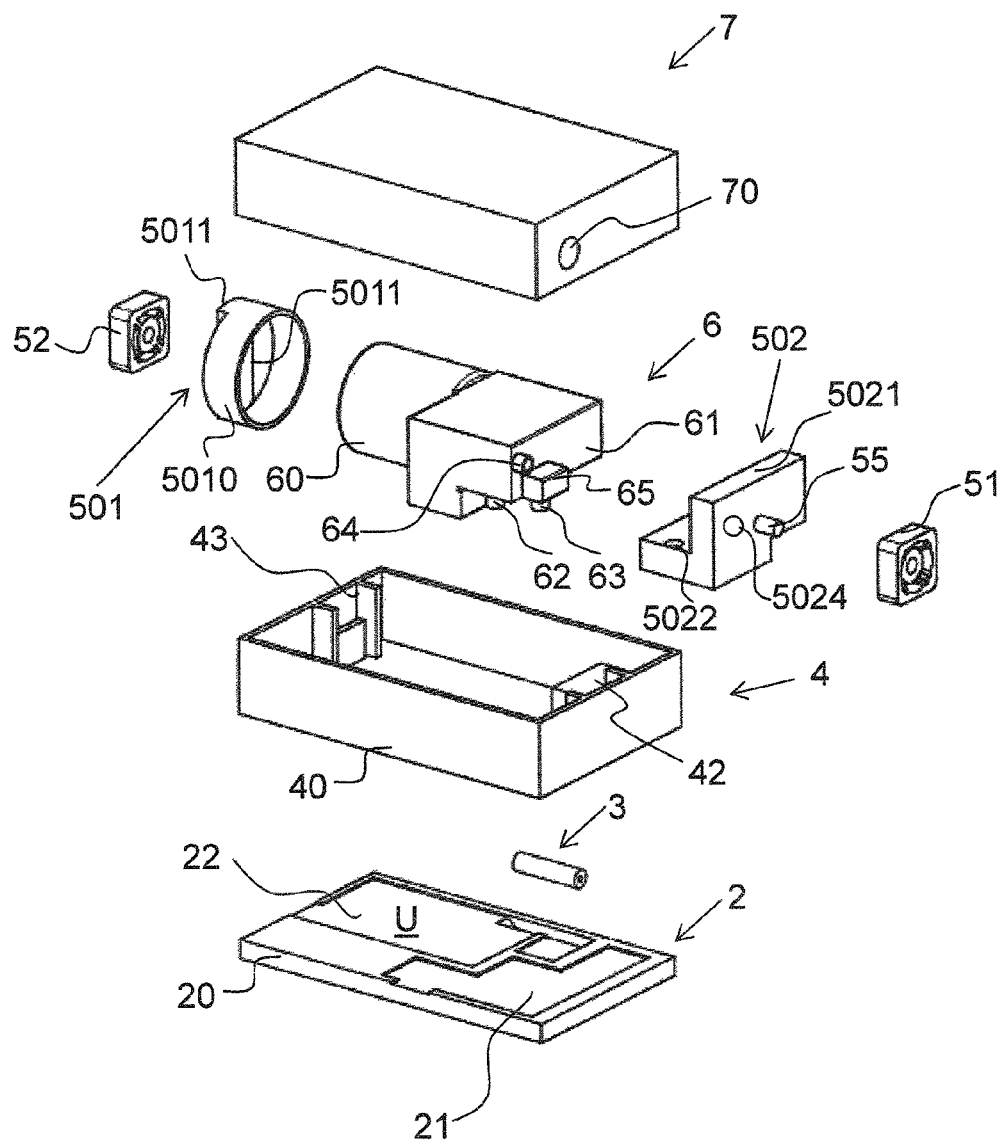
FIG. 9 shows a schematic view of a pump assembly and a pump assembly carrier according to a third embodiment of the invention.
Figure 11:
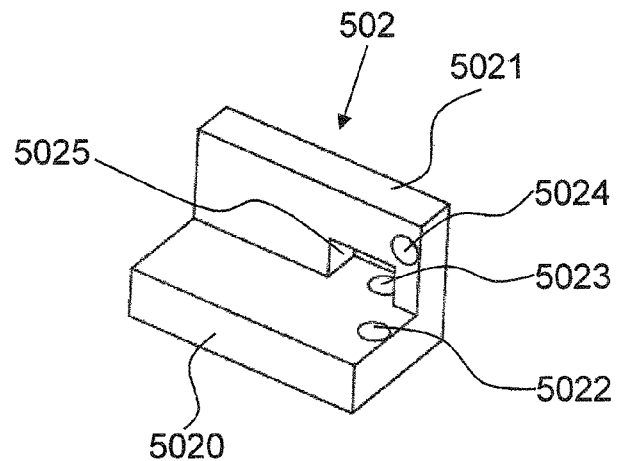
FIG. 11 shows a perspective view of a second pump assembly carrier part according to FIG. 9.
Figure 10:
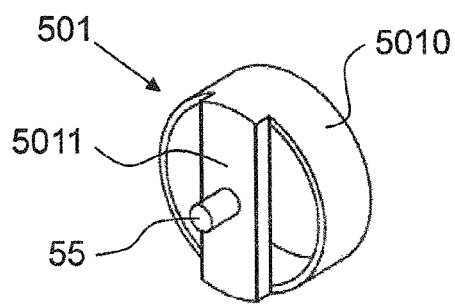
FIG. 10 shows a perspective view of a first pump assembly carrier part according to FIG. 9

FIGS. 9 to 11 show a third embodiment of the inventive device. The same parts are provided with the same reference signs as in the examples mentioned above and they are not described in detail anymore. The pump housing with the first pump housing part 1 and the second pump housing part 8 is not shown any more but is still present.

In this third embodiment, the pump assembly carrier is made of two parts. It comprises a first pump assembly carrier part 501 and a second pump assembly carrier part 502. They are arranged at two opposite ends of the pump assembly 6.

The first pump assembly carrier part 501 comprises a base body 5010 suitable for accommodating a motor 60. In this example, it is therefore shaped like a circular cylinder. One side is open for reception of the motor 60. The opposite side can have a closed shape. In this example, it has a partially closed shape, whereby a web 5011 extends over the diagonal. The protruding securing pin 55 is arranged on this web 5011, preferably in the middle. The securing pin 55 is used for holding the second bearing 52.

The second pump assembly carrier 502 is formed as a rectangular angular element. It comprises as a first leg a base 5020 and as a second leg a stop 5021. The vacuum assembly 61 lays on the base 5020. The base 5020 comprises a first through passage opening 5022 for reception of the nozzle of the exhaust air opening and a second through passage opening 5023 for reception of the nozzle of the ventilation opening 63. The stop 5021 comprises a third through passage opening 5024 for reception of the nozzle of the vacuum port 64 and a recess 5025 for reception of a protruding nose 65 of the vacuum assembly 61 in the region of the ventilation opening 63.

The side of the stop 5021 being opposite to the vacuum assembly 61 is also provided with a securing pin 55 used for holding the first bearing 51.

In this example, exactly two bearings 51, 52 are present. The first bearing seat 42 and the second bearing seat 43 are arranged accordingly in the first sound-damping housing part 4. In this example, they are thereby not laying on a parallel line to the longitudinal axis of the first sound-damping housing part 4, but they are arranged offset to each other, so that they enable a best possible uniform distribution of the weight of the pump assembly 6 on the two bearings 51, 52.

The invention is again explained below on the basis of the first illustrative embodiment according to FIGS. 1 to 7, the description also being applicable to the second and third example as well as to further illustrative embodiments within the meaning of the invention.

The first sound-damping housing part 4 is closed by the second sound-damping housing part 7. The closure is preferably effected such that no vibrations of any kind can occur between the housing parts 4, 7, or at least such that any vibrations cannot generate any sound. The former can be achieved by welding, for example, while the latter can be achieved by a suitably soft and sound-damping connection.

The sound-damping housing 4, 7 is preferably closed in an airtight manner, wherein a passage has to be present for the suction port or vacuum port. The latter is provided with reference sign 70 in FIG. 1. It connects the vacuum port 64 of the pump assembly 6 to a suction or vacuum hose via the vacuum port 80 of the pump housing 8, likewise visible in FIG. 1, or connects it directly to a breastshield or a fluid collection container.

In most vacuum pump assemblies, an air supply, i.e. ventilation, and an air withdrawal, i.e. an exhaust, is also needed. This air must therefore be able to be introduced into the closed sound-damping housing 4, 7 and must be able to flow out of the latter.

Figure 6:
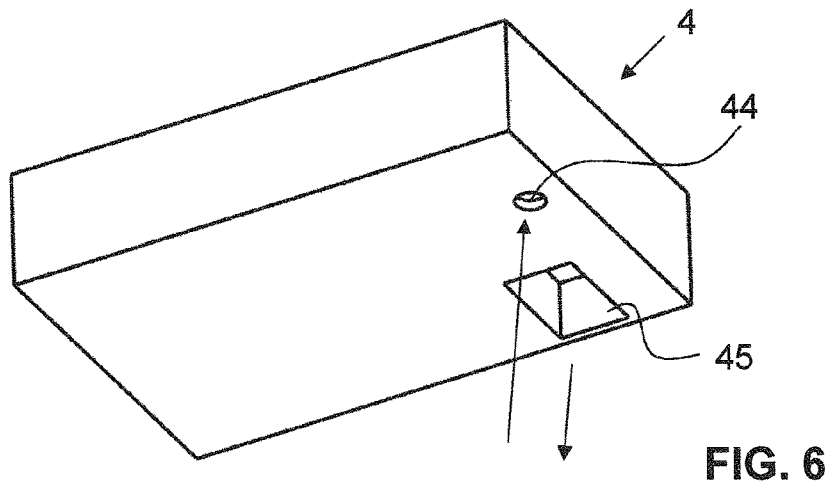
FIG. 6 shows a perspective bottom view of a first sound-damping housing part according to FIG. 1.

As is shown in FIG. 6, the first sound-damping housing part 4 therefore has a first passage 44 for the delivery of air for ventilation and a second passage 45 for the exhaust air flowing out. The second passage 45 is designed as a widened buffer space 450, as can be seen in FIG. 1.

Since the pump housing 1, 8 is not usually made airtight, it is not necessary to provide special air inlet and outlet openings in the pump housing 1, 8. However, they can be provided nonetheless if so required or desired.

In a simple embodiment, the inflowing and outflowing air is able to move without further guiding between the interior 11 of the pump housing 1, 8 and the sound-damping housing 4, 7.

However, in the embodiment presented here, the air exchange unit 2, also called gap system, is present. The air exchange unit 2 is preferably plate-shaped. It is preferably stiff, in particular produced from plastic. It is located on the underside of the first sound-damping housing part 4 and is connected to the latter in an airtight manner. In particular, it is adhesively bonded or welded thereto.

As is shown in FIG. 7, the air exchange unit 2 has a narrow, preferably stiff base plate 20, which is provided with an upwardly open ventilation channel 21 and a likewise upwardly open exhaust channel 22. The channels 21, 22 are closed by the connection to the first air damping housing part 4 shown in FIG. 6, wherein the ventilation channel 21 opens into the first passage 44 and the second passage 45 leads into the exhaust air channel 22.

The ventilation channel 21 begins at an inlet opening 24, which is created by a recess extending as far as the edge of the base plate 20. The outlet opening 25 of the exhaust air channel 24 is similarly made at another location. The channels 21, 22 are flat and thus have a relatively large volume. Moreover, the flow pressure of the exhaust air is reduced by the buffer space 450. The latter preferably opens into the buffer floor 220.

From the buffer floor 220, the exhaust air passes into a recessed channel in which an airstream sound damper 3, also called absorption damper, is arranged. The latter is preferably a silicone hose or tube through which the exhaust air passes. The airstream sound damper 3 can easily be inserted in the air exchange unit 2 or fixedly connected thereto, for example adhesively bonded or welded.

The exhaust air then passes into the outflow space 221, which has a relatively large surface area, and from there can flow outwards through the outlet opening.

To ensure that the noise development is minimized, at least the side walls 23 of the two channels 21, 22 are provided with a soft material. For example, a silicone layer is sprayed onto these side walls 23.

This airstream is usually not only necessary for the operation of the pump, but also contributes to cooling the pump assembly or serves as the single element for cooling.

The sound-damping housing 4, 7 now supplemented with the air exchange unit 2 is arranged in the pump housing 1, 8. For example, it can be fitted into a first pump housing part 10 and fixed in the usual way, e.g. by screwing and/or clamping. In addition to the sound-damping housing 4, 7, further elements are usually also arranged in the pump housing 1, 8, although these further elements are not shown here. These elements are, for example, accumulators and/or current transformers and electronic components.

The pump housing 1, 8 is preferably provided with lateral and lower support ribs 12, 13 and, if appropriate, also with upper spacer ribs, such that the sound-damping housing 4, 7 is held at a distance from the side walls of the pump housing.

The pump housing 1, 8 can have any desired shape. The sound-damping housing 4, 7 can also be of any desired shape. Pump housing 1, 8 and sound-damping housing 4, 7 are both preferably made from a stiff material, in particular from plastic.

By virtue of the flexible support, the suction pump according to the invention permits optimal sound damping.

| LIST OF REFERENCE SIGNS | |
|---|---|
| 1 | first pump housing part |
| 10 | first housing half-shell |
| 11 | interior |
| 12 | lateral support rib |
| 13 | lower support rib |
| 2 | air exchange unit |
| 20 | base plate |
| 21 | ventilation channel |
| 22 | exhaust air channel |
| 220 | buffer floor |
| 221 | outflow space |
| 23 | channel wall |
| 24 | inlet opening |
| 25 | outlet opening |
| 3 | airstream sound damper |
| 4 | first sound-damping housing part |
| 40 | first sound-damper half-shell |
| 41 | interior |
| 42 | first bearing seat |
| 420 | abutment |
| 43 | second bearing seat |
| 44 | first air passage |
| 45 | second air passage |
| 450 | buffer space |
| 5 | pump assembly carrier |
| 50 | motor seat |
| 501 | first pump assembly carrier part |
| 5010 | base body |
| 5011 | web |
| 502 | second pump assembly carrier part |
| 5020 | base |
| 5021 | stop |
| 5022 | first through passage opening |
| 5023 | second through passage opening |
| 5024 | third through passage opening |
| 5025 | recess |
| 51 | first bearing |

-continued

LIST OF REFERENCE SIGNS

| | |
|---|---|
| 52 | second bearing |
| 53 | gap |
| 54 | first abutment |
| 540 | first locking lug |
| 55 | securing pin |
| 56 | lateral abutment |
| 58 | assembly support |
| 580 | locking lug |
| 581 | balcony |
| 582 | bottom |
| 583 | opening |
| 59 | second abutment |
| 590 | second locking lug |
| 6 | pump assembly |
| 60 | motor |
| 61 | vacuum assembly |
| 62 | exhaust air opening |
| 63 | ventilation opening |
| 64 | vacuum port |
| 65 | nose |
| 7 | second sound-damping housing part |
| 70 | vacuum port |
| 8 | second pump housing part |
| 80 | vacuum port |

The invention claimed is:

1. A medical suction pump with a pump housing, with a pump assembly arranged in the pump housing and serving to generate an underpressure, and with a device for sound damping, wherein the device for sound damping has at least two elastic bearings for elastically supporting the pump assembly relative to the pump housing, wherein the at least two elastic bearings are arranged spaced apart from each other, and wherein the pump assembly is arranged in a sound-damping housing and is held elastically in relation to this sound-damping housing by means of the at least two elastic bearings, wherein the sound-damping housing is closed in an airtight manner except for a first air passage and a second air passage and except for a vacuum port.

2. The medical suction pump according to claim 1, wherein exactly two elastic bearings of these at least two elastic bearings are present.

3. The medical suction pump according to claim 1, wherein the at least two elastic bearings are formed from an elastomer.

4. The medical suction pump according to claim 1, wherein the pump assembly is suspended directly or indirectly in the pump housing exclusively by means of the at least two elastic bearings.

5. The medical suction pump according to claim 1, wherein a first elastic bearing and a second elastic bearing of these at least two elastic bearings are oriented in mutually opposite directions, and a third elastic bearing of these at least two elastic bearings is oriented in a further direction extending perpendicularly from said mutually opposite directions.

6. The medical suction pump according to claim 5, wherein the first elastic bearing and the second elastic bearing are arranged in the area of a vacuum assembly of the pump assembly, and the third elastic bearing is arranged in the area of a motor of the pump assembly.

7. The medical suction pump according to claim 1, wherein the at least two elastic bearings are held insertably in bearing seats.

8. The medical suction pump according to claim 1 wherein the at least two elastic bearings are elastomer bodies that can be plugged on.

9. The medical suction pump according to claim 1, wherein the pump assembly is held in a pump assembly carrier, and wherein the at least two elastic bearings are arranged on this pump assembly carrier.

10. The medical suction pump according to claim 9, wherein the pump assembly is held with pretensioning in the pump assembly carrier.

11. The medical suction pump according to claim 1, wherein an air exchange unit is present which delivers air to the pump assembly through the first air passage of the sound-damping housing and withdraws air from the pump assembly through the second air passage of the sound-damping housing.

12. The medical suction pump according to claim 1, wherein the sound-damping housing is arranged in a fixed position in the pump housing, and wherein the air exchange unit is arranged between pump housing and sound-damping housing.

13. The medical suction pump according to claim 1, wherein the air exchange unit is plate-shaped and has channels with channel walls, which are designed to damp sound.

14. The medical suction pump according to claim 13, wherein the channel walls are pliable.

15. The medical suction pump according to claim 1, wherein exhaust air withdrawn from the pump assembly is conveyed at least over part of a flow path through a tubular airstream sound damper.

16. The medical suction pump according to claim 1, wherein exactly three elastic bearings of these at least two elastic bearings are present.

17. A medical suction pump with a pump housing, with a pump assembly arranged in the pump housing and serving to generate an underpressure, and with a device for sound damping, wherein the device for sound damping has at least two elastic bearings for elastically supporting the pump assembly relative to the pump housing, wherein the at least two elastic bearings are arranged spaced apart from each other, and wherein the pump assembly is arranged in a sound-damping housing and is held elastically in relation to this sound-damping housing by means of the at least two elastic bearings, wherein the pump assembly is held in a pump assembly carrier, and wherein the at least two elastic bearings are arranged on this pump assembly carrier.

18. A medical suction pump with a pump housing, with a pump assembly arranged in the pump housing and serving to generate an underpressure, and with a device for sound damping, wherein the device for sound damping has at least two elastic bearings for elastically supporting the pump assembly relative to the pump housing, wherein the at least two elastic bearings are arranged spaced apart from each other, and wherein the pump assembly is arranged in a sound-damping housing and is held elastically in relation to this sound-damping housing by means of the at least two elastic bearings, wherein a first elastic bearing and a second elastic bearing of these at least two elastic bearings are oriented in mutually opposite directions, and a third elastic bearing of these at least two elastic bearings is oriented in a further direction extending perpendicularly from said mutually opposite directions.

19. The medical suction pump according to claim 18, wherein the first elastic bearing and the second elastic bearing are arranged in the area of a vacuum assembly of the pump assembly, and the third elastic bearing is arranged in the area of a motor of the pump assembly.

20. The medical suction pump according to claim 18, wherein the pump assembly is suspended directly or indirectly in the pump housing exclusively by means of the at least two elastic bearings.

21. A medical suction pump with a pump housing, with a pump assembly arranged in the pump housing and serving to generate an underpressure, and with a device for sound damping, wherein the device for sound damping has at least two elastic bearings for elastically supporting the pump assembly relative to the pump housing, wherein the at least two elastic bearings are arranged spaced apart from each other, and wherein the pump assembly is arranged in a sound-damping housing and is held elastically in relation to this sound-damping housing by means of the at least two elastic bearings, wherein exactly three elastic bearings of these at least two elastic bearings are present.

* * * * *